US012667267B2

(12) United States Patent
Hayashi et al.

(10) Patent No.: US 12,667,267 B2
(45) Date of Patent: Jun. 30, 2026

(54) METHOD, MEDICAL SYSTEM, AND COMPUTER READABLE MEDIUM

(71) Applicant: TERUMO KABUSHIKI KAISHA, Tokyo (JP)

(72) Inventors: Taiki Hayashi, Hadano Kanagawa (JP); Shinsuke Matsumoto, Sagamihara Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/792,192

(22) Filed: Aug. 1, 2024

(65) Prior Publication Data

US 2025/0040819 A1 Feb. 6, 2025

(30) Foreign Application Priority Data

Aug. 2, 2023 (JP) ................................. 2023-126519

(51) Int. Cl.
| | |
|---|---|
| *A61B 5/024* | (2006.01) |
| *A61B 5/00* | (2006.01) |
| *A61B 5/0255* | (2006.01) |

(52) U.S. Cl.
CPC ...... *A61B 5/02416* (2013.01); *A61B 5/02438* (2013.01); *A61B 5/0255* (2013.01); *A61B 5/7246* (2013.01); *A61B 5/7282* (2013.01)

(58) Field of Classification Search
CPC ............ A61B 5/02416; A61B 5/02438; A61B 5/0255; A61B 5/7246; A61B 5/7282; A61B 5/7203; A61B 5/7207
See application file for complete search history.

(56) References Cited

U.S. PATENT DOCUMENTS

| | | | | |
|---|---|---|---|---|
| 4,800,495 | A * | 1/1989 | Smith | A61B 5/7239 |
| | | | | 600/323 |
| 5,553,615 | A * | 9/1996 | Carim | A61B 5/7228 |
| | | | | 600/475 |
| 8,758,258 | B2 | 6/2014 | Takahashi et al. | |
| 10,485,429 | B2 * | 11/2019 | Lenehan | A61B 8/06 |
| 11,213,210 | B2 * | 1/2022 | Banerjee | A61B 5/02007 |
| 12,329,503 | B2 * | 6/2025 | Priem | A61B 5/14551 |
| 12,383,204 | B2 * | 8/2025 | Garrett | A61B 5/7203 |
| 2006/0074333 | A1 * | 4/2006 | Huiku | A61B 5/0205 |
| | | | | 600/301 |

(Continued)

FOREIGN PATENT DOCUMENTS

| | | | |
|---|---|---|---|
| JP | 2010-172645 A | 8/2010 | |

*Primary Examiner* — Oommen Jacob
(74) *Attorney, Agent, or Firm* — Kim & Stewart LLP

(57) ABSTRACT

A method for obtaining photoplethysmographic data suitable for medical measurement, includes emitting light from a photoplethysmographic sensor toward a body of a patient, and converting the light reflected by or passing through the body and received by the sensor for a particular period into a voltage signal indicating variation of voltage in the period, calculating a score for each of one or more portions of the voltage signal using voltage values thereof, generating data corresponding to one of the portions, the score of which satisfies a predetermined condition, and storing in a memory the generated data as the photoplethysmographic data suitable for the medical measurement.

14 Claims, 11 Drawing Sheets

1

(56)             References Cited

U.S. PATENT DOCUMENTS

2012/0108928 A1*   5/2012   Tverskoy ............. A61B 5/0059
                                                              600/324
2014/0276119 A1*   9/2014   Venkatraman ..... A61B 5/02405
                                                              600/509
2015/0088431 A1*   3/2015   Podhajsky ............. A61B 5/443
                                                              600/479
2015/0313477 A1*   11/2015  Maarek ................ A61B 5/0205
                                                              600/301
2016/0206213 A1*   7/2016   Maarek ............. A61B 5/02416
2017/0156606 A1*   6/2017   Ferber ................. A61B 5/6824
2018/0160905 A1*   6/2018   Wang ................. A61B 5/7264
2018/0279953 A1*   10/2018  Wang .................... A61B 5/318
2018/0317785 A1*   11/2018  MacDonald ....... A61B 5/02438
2018/0325457 A1*   11/2018  Ghosh ................... A61B 5/352
2025/0040819 A1*   2/2025   Hayashi ............. A61B 5/7282
2025/0040820 A1*   2/2025   Hayashi ................ G16H 40/67

* cited by examiner

FIG. 6

METHOD, MEDICAL SYSTEM, AND COMPUTER READABLE MEDIUM

CROSS-REFERENCE TO RELATED APPLICATION(S)

This application is based on and claims the benefit of priority from Japanese patent application No. 2023-126519, filed Aug. 2, 2023, the entire contents of which are incorporated herein by reference.

BACKGROUND

Technical Field

Embodiments described herein relate generally to a method, a medical system, and a computer readable medium.

Related Art

Cardiac diseases such as heart failure, malignant neoplasms, and stroke are referred to as three major diseases. Since the prognoses of patients who have suffered from heart failure are not good, it is necessary to continuously monitor their conditions in healthcare facilities. Patients who have suffered from heart failure tend to have faster pulse rates than those of healthy people in order to deliver sufficient amounts of blood throughout their bodies.

To measure photoplethysmographic signals, patients' fingertips, earlobes, or other body parts are irradiated with light from a light source such as an LED, and then the irradiated light is compared with the transmitted or reflected light. Using the photoplethysmographic signals in this manner enables medical workers to measure the patients' blood volumes and pulse rates.

There is a known technique for using a pulse wave sensor utilizing photoplethysmographic signals and an acceleration sensor to detect a user's pulse wave signal and body motion signal. The detected pulse wave signal is then subjected to a noise removal process, based on the detected body motion signal, so that the user's pulse wave can be extracted.

SUMMARY

Embodiments of the present disclosure provide a method and a medical system capable of extracting, from a photoplethysmographic signal, a signal in which a pulse wave has been appropriately measured.

According to one embodiment, a method for obtaining photoplethysmographic data suitable for medical measurement comprises: emitting light from a photoplethysmographic sensor toward a body of a patient, and converting the light reflected by or passing through the body and received by the sensor for a particular period into a voltage signal indicating variation of voltage in the period; calculating a score for each of one or more portions of the voltage signal using voltage values thereof; generating data corresponding to one of the portions, the score of which satisfies a predetermined condition; and storing in a memory the generated data as the photoplethysmographic data suitable for the medical measurement.

According to the above embodiment, it is possible to extract, from a photoplethysmographic signal, a signal in which a pulse wave has been appropriately measured.

BRIEF DESCRIPTION OF DRAWINGS

FIG. 6 is a diagram illustrating an example of a method of calculating a third score.

DETAILED DESCRIPTION

Figure 1:
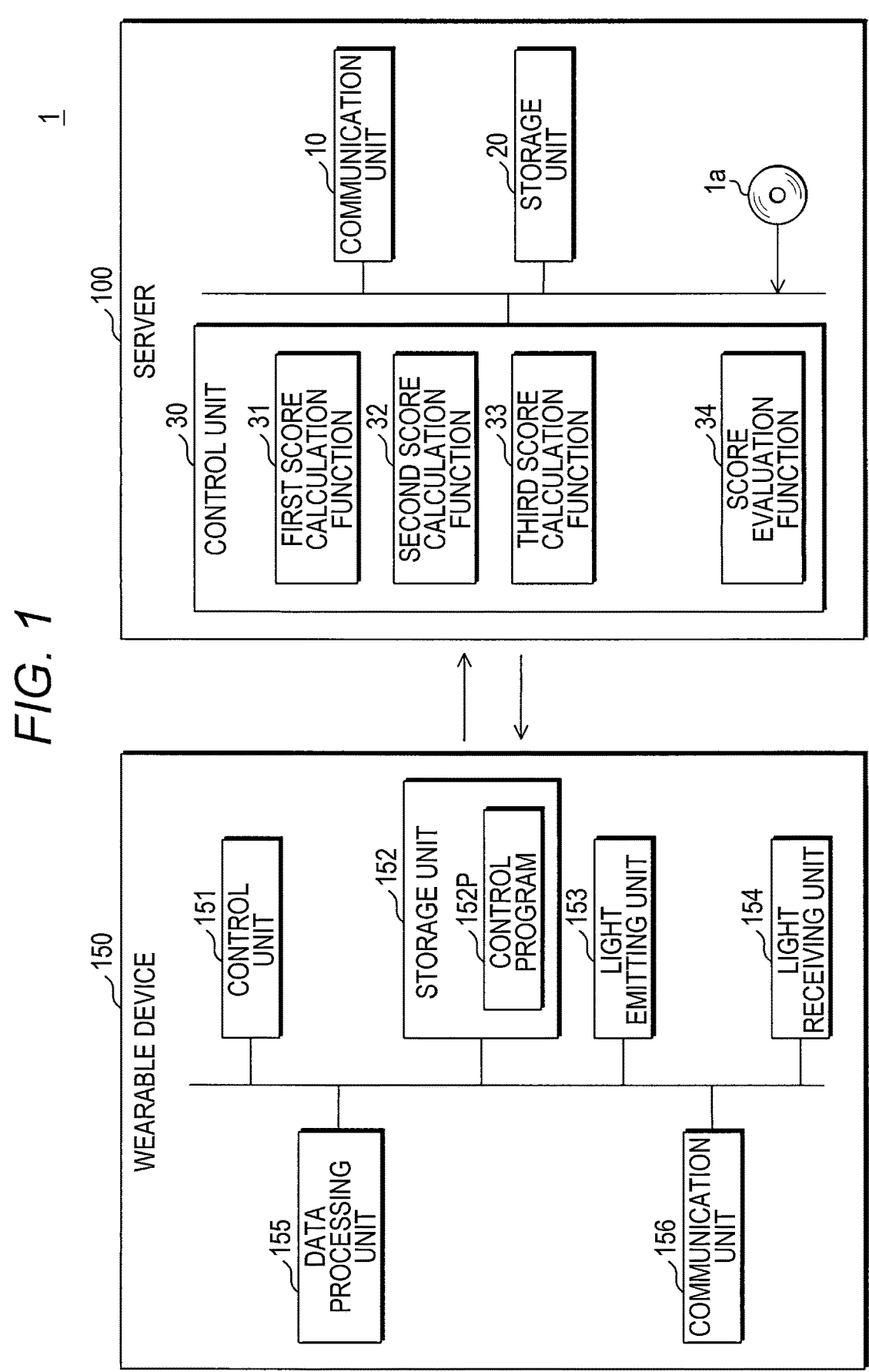
FIG. 1 is a diagram illustrating a configuration example of an accuracy score calculation system for photoplethysmographic signals.

Embodiments of this disclosure will be described below in detail, with reference to the drawings. FIG. 1 is a diagram illustrating a configuration example of an accuracy score calculation system 1 for photoplethysmographic signals according to one embodiment. The accuracy score calculation system 1 is a medical system that acquires a user's photoplethysmographic signal, calculates scores in relation to the acquired photoplethysmographic signal, and then extracts, from the photoplethysmographic signal, a portion (i.e., a partial signal) in which the calculated scores satisfy conditions for predetermined thresholds. The accuracy score calculation system 1 according to the present embodiment includes a wearable device 150 and a server 100. Both the wearable device 150 and the server 100 are interconnected via a communication network.

The wearable device 150 includes a control unit 151, a storage unit 152, a light emitting unit 153, a light receiving unit 154, a data processing unit 155, and a communication unit 156, all of which are interconnected via a bus. The wearable device 150 measures a user's photoplethysmographic signal and then transmits the measured photoplethysmographic signal to the server 100.

In the present embodiment, the wearable device 150 will be described as an example of a photoplethysmographic sensor; however, the photoplethysmographic sensor is not limited to such a wearable device.

Measuring instruments for photoplethysmographic signals are classified into two types: a transmission type and a reflection type. The transmission type has a mode in which the light emitting unit 153 and the light receiving unit 154 are disposed with a user's fingertip, earlobe, or other body part therebetween. In this transmission type, the light emitting unit 153 irradiates the user's fingertip, earlobe, or other body part with red light or other colored light, and then the light receiving unit 154 detects the red light or other colored light transmitted through the user's fingertip, earlobe, or other body part. The reflection type has a mode in which the light emitting unit 153 and the light receiving unit 154 are disposed adjacent to each other. In this reflection type, the light emitting unit 153 irradiates a user's body surface with red light, green light, and other colored light, and then the light receiving unit 154 detects the red light, the green light, and other colored light reflected on the interior of the user's living body.

In the present embodiment, only an example in which the reflection type is used will be described; however, the transmission type may be used.

The control unit 151 is a controller or a control circuit that includes one or more processors, including a central processing unit (CPU), a micro processing unit (MPU), and a graphics processing unit (GPU). Alternatively, the control unit 151 may be formed of the combination of a digital signal processor (DSP), a field programmable gate array (FPGA), and some other components. The control unit 151 reads and executes a control program 152P stored in the storage unit 152. Then, the control unit 151 performs various information processes, control processes, and other processes related to the wearable device 150, thereby controlling the storage unit 152, the light emitting unit 153, the light receiving unit 154, the data processing unit 155, and the communication unit 156.

The storage unit 152 is a memory that includes a static random access memory (SRAM), a dynamic random access memory (DRAM), and a flash memory. The storage unit 152 temporarily stores data needed by the control program 152P and the control unit 151 to perform arithmetic processes.

The light emitting unit 153 includes an LED light source having a wavelength region covering those of red light, green light, and other colored light. In addition, the light emitting unit 153 may further include other LED light sources having different wavelength regions. By using the light emitting unit 153, the control unit 151 irradiates a user's body surface or other body part with the light.

The light receiving unit 154 includes a photodiode and an infrared cut filter. The photodiode detects reflected light of the LED light with which the light emitting unit 153 has irradiated the user and then converts the detected reflected light into an electrical signal. The infrared cut filter reduces the influence of ambient light, such as infrared light, which might be detected by the photodiode.

The data processing unit 155 includes a signal amplifier, an analog-to-digital (AD) converter, and a microcomputer. The signal amplifier amplifies the electrical signal that has been converted by the light receiving unit 154. The AD converter AD converts the amplified electrical signal. The microcomputer performs various arithmetic processes to acquire a photoplethysmographic signal from the converted electrical signal.

Alternatively, the control unit 151 may control the communication unit 156 to transmit, to the server 100, the electrical signal that has been converted by the data processing unit 155. In this case, the server 100 may convert the electrical signal that has been converted by the wearable device 150 into the photoplethysmographic signal.

The communication unit 156 is a network interface circuit that transmits the photoplethysmographic signal to the server 100. Although a single wearable device 150 is illustrated in FIG. 1, a plurality of wearable devices 150 may be present for respective target users.

The communication unit 156 may add an identifier (ID) to the photoplethysmographic signal before transmitting the photoplethysmographic signal to the server 100. In this case, the identifier may contain a plurality of characters, numbers, and some other signs indicating information, such as a user name and a date and time when the photoplethysmographic signal is acquired.

The server 100 includes a communication unit 10, a storage unit 20, and a control unit 30.

In the present embodiment, the server 100 will be described as an example of an information processing apparatus; however, the information processing apparatus is not limited to such a server.

The communication unit 10 is a network interface circuit for communicating with the wearable device 150. The communication unit 10 receives, via the communication network, the user's photoplethysmographic signal that has been transmitted by the wearable device 150. The communication unit 10 can transmit or receive information to or from the wearable device 150 through wired communication using a cable.

The storage unit 20 includes a static random access memory (SRAM), a dynamic random access memory (DRAM), and a flash memory. The storage unit 20 acquires, in advance, various types of data needed by the control unit 30 to perform processes. The storage unit 20 stores data and other information that has been generated when the control unit 30 performs various processes.

The control unit 30 is a controller or a control circuit that includes one or more processors, including a central processing unit (CPU), a micro processing unit (MPU), and a graphics processing unit (GPU). Furthermore, the control unit 30 may be formed of the combination of digital signal processors (DSPs), field-programmable gate arrays (FPGAs), and some other components. The control unit 30 includes a semiconductor memory, such as a flash memory, and stores computer programs. The control unit 30 can execute a computer program loaded onto the semiconductor memory. Such computer programs may be downloaded from an external device via the communication unit 10 and stored in the semiconductor memory. Furthermore, the control unit 30 may read computer programs stored in a storage medium 1a (e.g., an optically readable disk storage medium, such as a compact disc-read-only memory (CD-ROM)) and then may store the read computer programs in the semiconductor memory. Alternatively, the computer programs may be stored in the storage unit 20, which is a hard disk. In this case, the computer program can be installed so as to be executable on a single computer or on a plurality of computers disposed at a single site or distributed across a plurality of sites and interconnected by a communication network.

The control unit 30 removes specific frequency band components contained in the photoplethysmographic signal with an existing technique using a low-pass filter, a high-pass filter, a band-pass filter, and some other elements. Details of this technique will not be described below.

The control unit 30 performs a first score calculation function 31, a second score calculation function 32, a third score calculation function 33, and a score evaluation function 34. Details of these functions will be described later.

Figure 2:
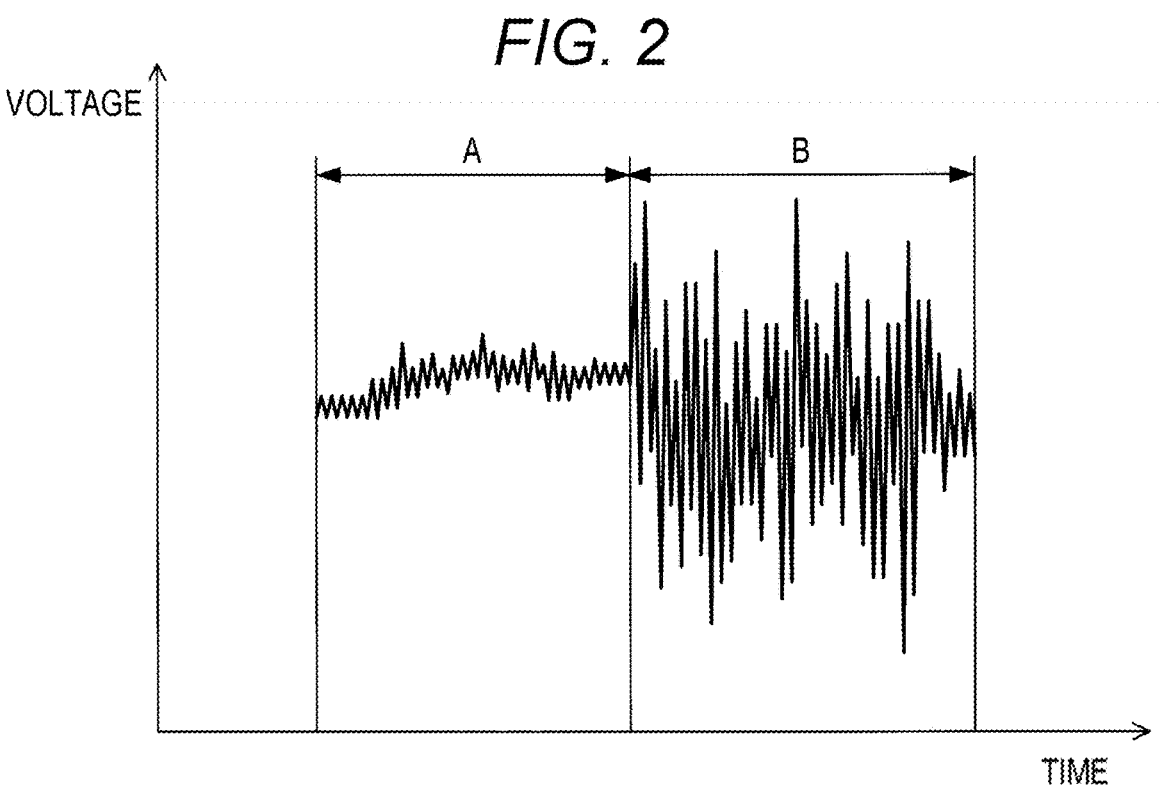
FIG. 2 is a diagram illustrating an example of a photoplethysmographic signal acquired by a wearable device.

FIG. 2 is a diagram illustrating an example of a photoplethysmographic signal acquired by the wearable device 150. As shown in FIG. 2, this photoplethysmographic signal contains: a signal waveform portion, i.e., segment A, that is less subject to external factors such as body motion and ambient light; and a signal waveform portion, i.e., segment B, that is more subject to the body motion and other external factors. In this graph, the vertical axis represents the voltage of the photoplethysmographic signal (i.e., light intensity of the received LED light), and the horizontal axis represents the measurement time.

In the present embodiment, the server 100 acquires a user's photoplethysmographic signal from the wearable device 150 and then extracts feature amounts of a pulse rate and other medical data from the acquired photoplethysmographic signal. If the influence of external factors, such as the body motion, is prominent as in segment B of FIG. 2, the photoplethysmographic signal contains large amounts of noise, in which case it is difficult to appropriately extract the pulse rate and some other medical data from the photoplethysmographic signal.

In the above case, conventionally, one or more additional sensors, such as an acceleration sensor, are used to identify and exclude a portion influenced by the body motion or some other external factors. However, using such a large number of sensors leads to increased cost and power consumption.

In the present embodiment, some scores indicating whether a pulse wave has been appropriately measured are calculated from the photoplethysmographic signal itself. Then, a signal waveform portion in which each of the calculated scores satisfies a condition for a preset threshold is extracted as a portion in which the pulse wave has been appropriately measured.

More specifically, as described below, the server 100 calculates three scores (i.e., first to third scores) from the photoplethysmographic signal and then extracts data on a signal waveform portion in which each score satisfies a condition for a preset threshold.

First, a procedure for calculating the first score will be described below.

The first score calculation function 31 of the control unit 30 measures the degree to which the acquired photoplethysmographic signal is distorted and then calculates a distorted proportion of the photoplethysmographic signal, as the first score.

Figure 3:
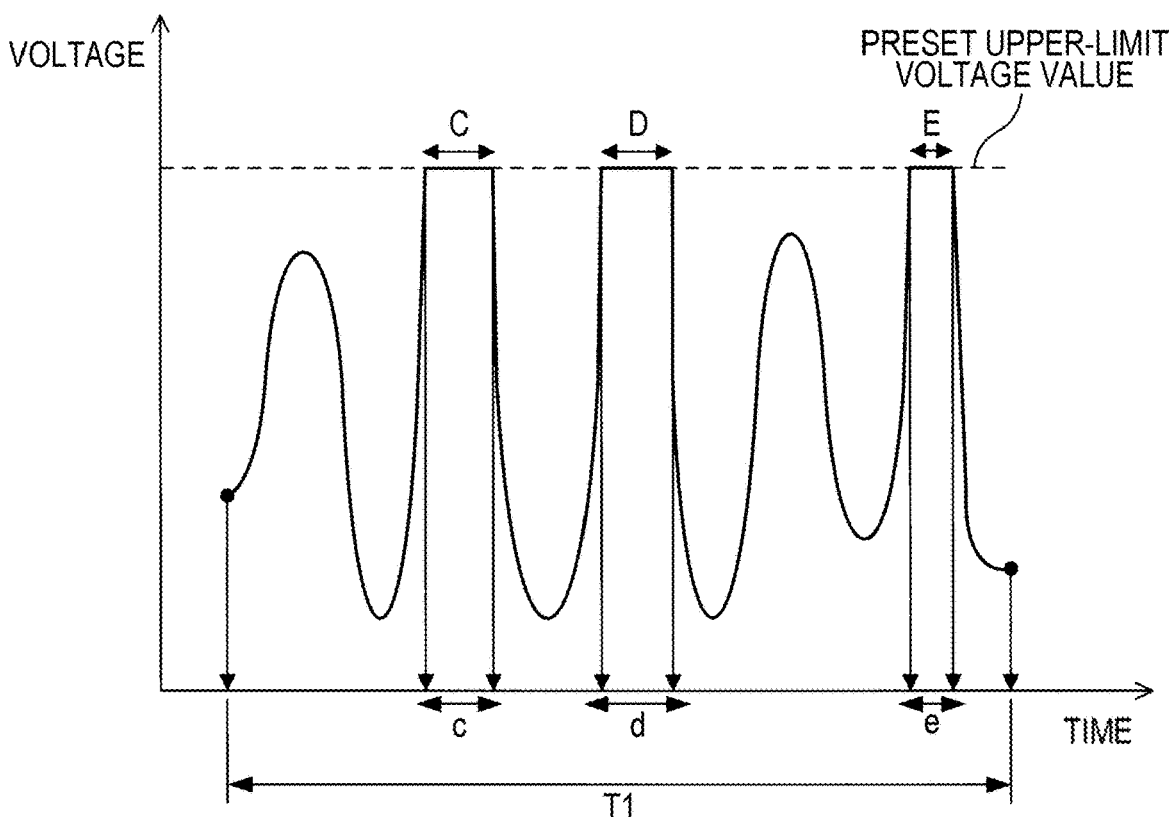
FIG. 3 is a diagram illustrating an example of a method of calculating a first score.

FIG. 3 is a diagram illustrating an example of a method of calculating the first score. Further, FIG. 3 illustrates a photoplethysmographic signal acquired by the wearable device 150 and a preset upper-limit voltage value (i.e., an intensity threshold of received light intensity). In this graph, the vertical axis represents the voltage, and the horizontal axis represents the measurement time.

The photoplethysmographic signal illustrated in FIG. 3 is formed from, for example, ambient light and the reflected light of the LED light with which the user is irradiated. As the output of the LED light emitted from the light emitting unit 153 increases, the reflected light of the LED light with which the user is irradiated increases. Consequently, the light receiving unit 154 can detect large amounts of reflected light of the LED light emitted from the light emitting unit 153, compared to the ambient light.

However, when the output of the reflected light of the LED light with which the user is irradiated exceeds the preset upper-limit voltage value, distortions of the photoplethysmographic signal are detected. For example, the distortions of the photoplethysmographic signal correspond to segments C, D, and E in which the signal waveform is partly rectangular. In short, the photoplethysmographic signal is distorted when the voltage value of the photoplethysmographic signal exceeds a measurable upper-limit voltage value, namely, an intensity threshold of the received light intensity.

It should be noted that the intensity threshold of the received light intensity may be set to be lower than the upper-limit value, instead of being equated with the upper-limit value.

The first score calculation function 31 calculates the degree to which the photoplethysmographic signal is distorted, as the first score.

In FIG. 3, the first score calculation function 31 identifies portions C, D, and E of the photoplethysmographic signal, the voltage values of which are higher than the preset upper-limit voltage value. The first score calculation function 31 then calculates times c, d, and e over which the voltage value of the photoplethysmographic signal is more than the voltage upper-limit value, based on the time at which the photoplethysmographic signal is acquired. The first score calculation function 31 then divides the total time over which the voltage value of the photoplethysmographic signal is more than the upper-limit voltage value by a total time (T1) over which the photoplethysmographic signal is measured. The control unit 30 calculates a value acquired by the division, as the first score. More specifically, in FIG. 3, the first score is calculated as $(c+d+e)/T1$. In this case, a higher first score indicates larger amounts of distortions of the photoplethysmographic signal; in other words, a lower first score indicates smaller amounts of distortions of the photoplethysmographic signal. Therefore, a case where the first score satisfies the condition for the predetermined threshold can be regarded as a case where the first score is less than the preset threshold.

Alternatively, the first score calculation function 31 may acquire the photoplethysmographic signal as a signal waveform image and then may calculate the first score by using the acquired signal waveform image. In this case, the first score calculation function 31 may acquire, as the size of the image (i.e., the number of pixels in the image), the total time over which the photoplethysmographic signal is measured and the total time over which the voltage value of the photoplethysmographic signal exceeds the preset upper-limit voltage value from the signal waveform image. The first score calculation function 31 performs the above process based on the size of the acquired image, thereby calculating the first score.

With the above configuration, the first score calculation function 31 can calculate the degree to which the photoplethysmographic signal is distorted, as the first score.

Next, a procedure for calculating the second score will be described below.

The second score calculation function 32 of the control unit 30 performs autocorrelation analysis, based on the photoplethysmographic signal and an envelope curve derived from the photoplethysmographic signal. The second score calculation function 32 then uses an autocorrelation coefficient calculated by the autocorrelation analysis to determine a second score by which periodicity synchronized with a pulsation of the photoplethysmographic signal is to be evaluated.

Figure 4A:
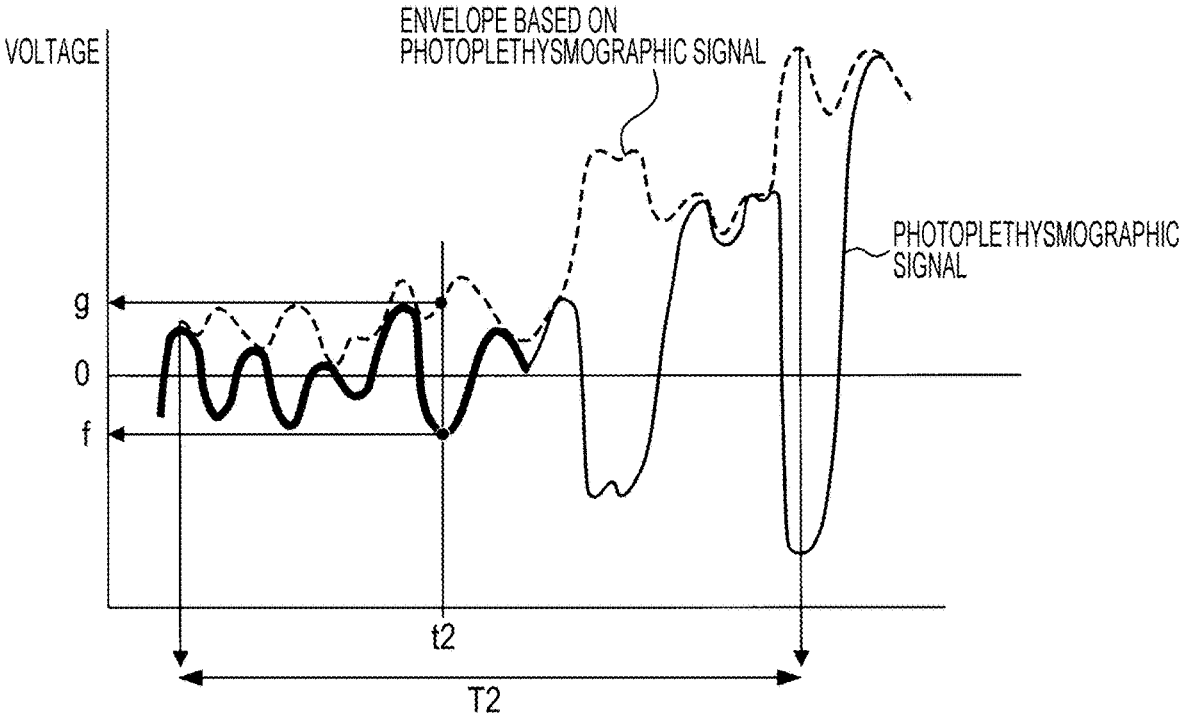
FIGS. 4A and 4B are diagrams illustrating an example of a method of calculating a second score.
Figure 4B:
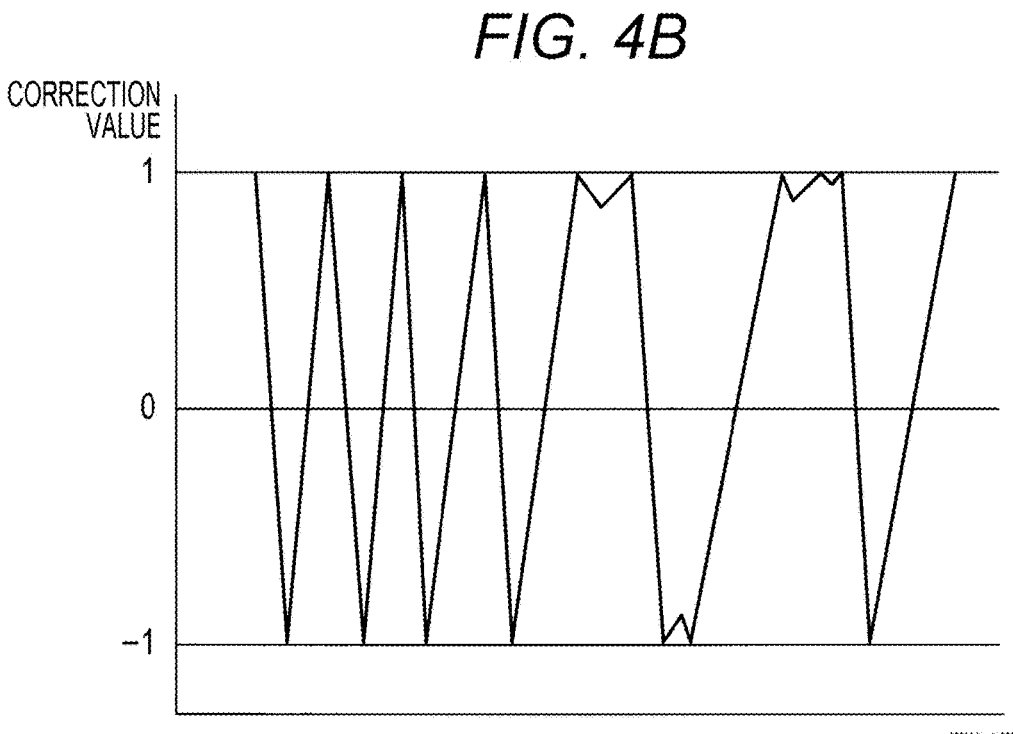

FIGS. 4A and 4B are diagrams illustrating an example of a method of calculating the second score. FIG. 4A contains a photoplethysmographic signal and an envelope curve based on the photoplethysmographic signal. Further, FIG. 4A illustrates: a signal waveform portion (i.e., a thick-line segment in FIG. 4A) that is less subject to external factors, such as body motion and ambient light; and another signal waveform portion (i.e., a segment other than the thick-line segment) that is more subject to the body motion and some other external factors. In FIG. 4A, the photoplethysmographic signal is indicated by the solid line, and the envelope curve based on the photoplethysmographic signal is indicated by a dotted line. In the graph of FIG. 4A, the vertical axis represents the voltage values of the photoplethysmographic signal and the envelope curve based on the photoplethysmographic signal, and the horizontal axis represents the measurement time.

The photoplethysmographic signal indicates, as a signal waveform, variations in the volume of a blood vessel which are generated when the heart delivers blood throughout the body. Therefore, the photoplethysmographic signal tends to exhibit periodicity synchronized with the pulsation within a signal waveform portion in which the influence of external factors, such as body motion and ambient light, is less prominent. However, the photoplethysmographic signal may fail to exhibit the periodicity synchronized with the pulsation within a signal waveform portion in which the influence of body motion and other factors are more prominent because the influence of external factors causes noise to be added to the signal waveform.

Autocorrelation analysis is used as a method of evaluating whether a photoplethysmographic signal has periodicity synchronized with pulsation. In this autocorrelation analysis, autocorrelation coefficients are calculated in relation to an amount (hereinafter referred to as a lag) shifted by a certain time from the original data.

The second score calculation function 32 calculates the sum of the autocorrelation coefficients for the respective lags. When the photoplethysmographic signal has periodicity synchronized with the pulsation, the sum of the autocorrelation coefficients increases. More specifically, when the photoplethysmographic signal has periodicity synchronized with the pulsation, the autocorrelation coefficient for each lag increases at a constant period, so that the sum of the autocorrelation coefficients also increases.

When the photoplethysmographic signal does not have periodicity synchronized with the pulsation, the sum of the autocorrelation coefficients decreases. More specifically, when the photoplethysmographic signal does not have periodicity synchronized with the pulsation, the autocorrelation coefficient for each lag generally decreases, so that the sum of the autocorrelation coefficients also decreases.

However, there are cases where not only the periodicity of the signal waveform itself but also the amplitude of the photoplethysmographic signal periodically changes within a signal waveform portion in which the influence of body motion and some other external factors is prominent. In such cases, the autocorrelation coefficient for each lag may increase regardless of whether the periodicity of the photoplethysmographic signal is synchronized with the pulsation. Thus, the control unit 30 may have difficulty determining whether the photoplethysmographic signal has periodicity synchronized with the pulsation simply by evaluating the sum of the calculated autocorrelation coefficients.

To deal with the above disadvantage, the second score calculation function 32 generates an envelope curve based on the photoplethysmographic signal as illustrated in FIG. 4A. The envelope curve is generated, for example, by rectifying and smoothing the photoplethysmographic signal or by performing Hilbert transform thereon. However, there are no limitations on a method of generating such an envelope curve. The second score calculation function 32 acquires voltage values f and g from the photoplethysmographic signal and the envelope curve at a specific time t2. The second score calculation function 32 then divides the voltage value f of the photoplethysmographic signal at the specific time t2 by the voltage value g of the envelope curve at the specific time. Through the above process, the second score calculation function 32 calculates a value (hereinafter referred to as a correction value) obtained by dividing the voltage value of the photoplethysmographic signal by the voltage value of the envelope curve. More specifically, at time t2 in FIG. 4A, the correction value is calculated as f/g. The second score calculation function 32 calculates the correction values for respective times within a period T2 over which the photoplethysmographic signal is measured.

FIG. 4B is an example of a graph showing the correction values for the respective times at which the photoplethysmographic signal is detected. In the graph of FIG. 4B, the vertical axis represents the correction value, and the horizontal axis represents the measurement time. The envelope curve based on the photoplethysmographic signal touches the positive amplitude of the photoplethysmographic signal at some times. This means that the voltage value of the envelope curve is always more than or equal to the voltage value of the photoplethysmographic signal. The correction value calculated by dividing the voltage value of the photoplethysmographic signal by the voltage value of the envelope curve always falls within a range from −1 to +1.

The second score calculation function 32 performs the autocorrelation analysis by using the correction value for each time illustrated in FIG. 4B. More specifically, the second score calculation function 32 calculates the autocorrelation coefficients for respective lags by using the correction value for each time illustrated in FIG. 4B. The second score calculation function 32 then calculates the sum (i.e., second score) of the autocorrelation coefficients for the respective lags. In this way, the second score calculation function 32 calculates the autocorrelation coefficients from the correction values obtained from the generated envelope curve. This can reduce the influence of external factors such as ambient light and body motion, thus facilitating the evaluation of the periodicity synchronized with the pulsation of the photoplethysmographic signal.

When the photoplethysmographic signal contains periodicity synchronized with the pulsation, the sum (i.e., the second score) of the autocorrelation coefficients increases. In other words, when the photoplethysmographic signal contains no periodicity synchronized with pulsation, the sum of the autocorrelation coefficients decreases. Therefore, a case where the condition for the predetermined threshold in the second score is satisfied can be regarded as a case where the second score is more than a preset threshold.

With the above configuration, the second score calculation function 32 calculates the correction values from both the photoplethysmographic signal and the envelope curve based on the photoplethysmographic signal. The second score calculation function 32 then calculates the autocorrelation coefficient for each lag by performing the autocorrelation analysis based on the calculated correction values. The second score calculation function 32 then calculates the sum of the autocorrelation coefficients for the respective lags as a second score.

Next, a procedure for calculating the third score will be described below.

The photoplethysmographic signal, as illustrated in FIG. 2, acquired from the user contains: a signal waveform portion that is more subject to external factors such as body motion and ambient light; and another signal waveform portion that is less subject to the body motion and other external factors. When a photoplethysmographic signal containing many signal waveform portions that are less subject to external factors is acquired, the control unit 30 can easily extract a pulse rate and some other medical data from this photoplethysmographic signal.

The third score calculation function 33 of the control unit 30 generates a template of a pulse wave for use in extracting a signal waveform portion that is less subject to external factors from a user's photoplethysmographic signal, based on a noiseless photoplethysmographic signal prepared in advance (e.g., a photoplethysmographic signal measured in the past from a user). The third score calculation function 33 separates the user's photoplethysmographic signal into individual pulses. For example, each pulse may correspond to a segment present between two adjacent valleys in the photoplethysmographic signal. The third score calculation function 33 compares the template with each separated pulse. As a result of the above comparison, the third score calculation function 33 extracts, from the separated pulses, pulses (hereinafter referred to as high-precision pulses) each of which has a high correlation coefficient with the template. The third score calculation function 33 calculates, as the third score, a proportion of the high-precision pulses to all the separated pulses.

A method of generating the template will be described below.

Figure 5A:
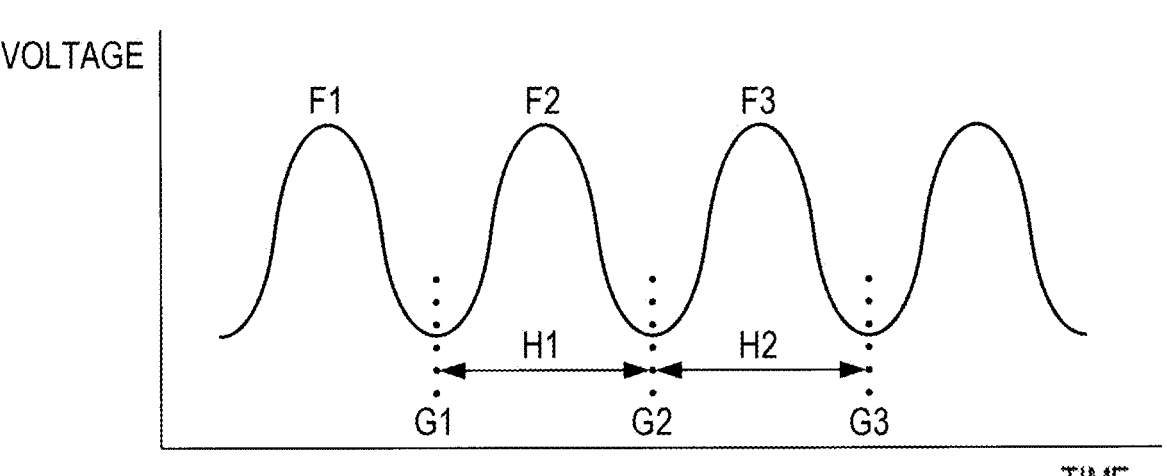
FIGS. 5A and 5B are diagrams illustrating an example of a method of generating a template.
Figure 5B:
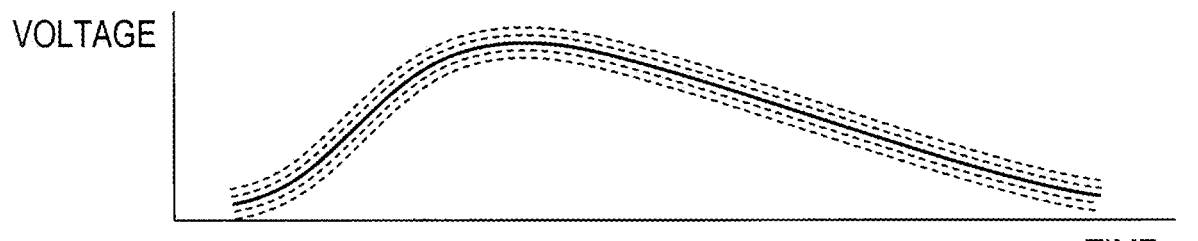

FIGS. 5A and 5B are diagrams illustrating an example of a method of generating the template. FIG. 5A is a diagram illustrating a noiseless photoplethysmographic signal prepared in advance. The noiseless photoplethysmographic signal is extracted, based on predetermined criteria, from photoplethysmographic signals that have been pre-acquired via a network. The predetermined criteria are set based on domain knowledge and medical viewpoints, for example. In the graph of FIG. 5A, the vertical axis and the horizontal axis represent the same factors as those of FIG. 2. In the photoplethysmographic signal illustrated in FIG. 5A, a plurality of peaks F1, F2, and F3 and a plurality of valleys G1, G2, and G3 are illustrated. For example, each peak corresponds to a portion having the highest voltage (i.e., electric potential) in a wavelength of the photoplethysmographic signal. For example, each valley corresponds to a portion having the lowest voltage present between two adjacent peaks in the photoplethysmographic signal.

The third score calculation function 33 processes the photoplethysmographic signal as illustrated in FIG. 5A with a band pass filter. The third score calculation function 33 then separates the photoplethysmographic signal into a plurality of pulses, each of which corresponds to a segment H1 or H2 present between two adjacent valleys. The third score calculation function 33 then normalizes the separated pulses. As a result of the normalization, for example, the voltage value of each pulse is converted into a range of 0 to 1, whereas the time when each pulse is acquired is converted into a range of 0 to 100.

FIG. 5B is a diagram illustrating normalized pulses and the template. In the graph in FIG. 5B, the vertical axis represents the voltage value of each normalized pulse, and the horizontal axis represents the time when each normalized pulse is acquired. In FIG. 5B, the plurality of pulses generated as a result of the normalization process is indicated by dotted lines. In FIG. 5B, the template is indicated by a solid line. The third score calculation function 33 calculates an average value, a median value, and some other statistical values of pulses from the plurality of normalized pulses. The third score calculation function 33 generates the template by using the average value, the median value, or the other statistical values of the pulses.

Before generating the template, the third score calculation function 33 may exclude some of the normalized pulses which largely deviate from the average value, the median value, or the other statistical values of the pulses. In this case, the third score calculation function 33 may use a quartile range, for example, to identify pulses deviating from the average value, the median value, or the other statistic pulse values, from the plurality of normalized pulses and then may exclude the identified pulses therefrom.

The third score calculation function 33 may generate a plurality of templates, depending on the time period of a day (e.g., daytime or nighttime). In this case, the third score calculation function 33 may be able to easily identify a photoplethysmographic signal that is less subject to external factors by comparing the photoplethysmographic signal with each template.

Figure 6:
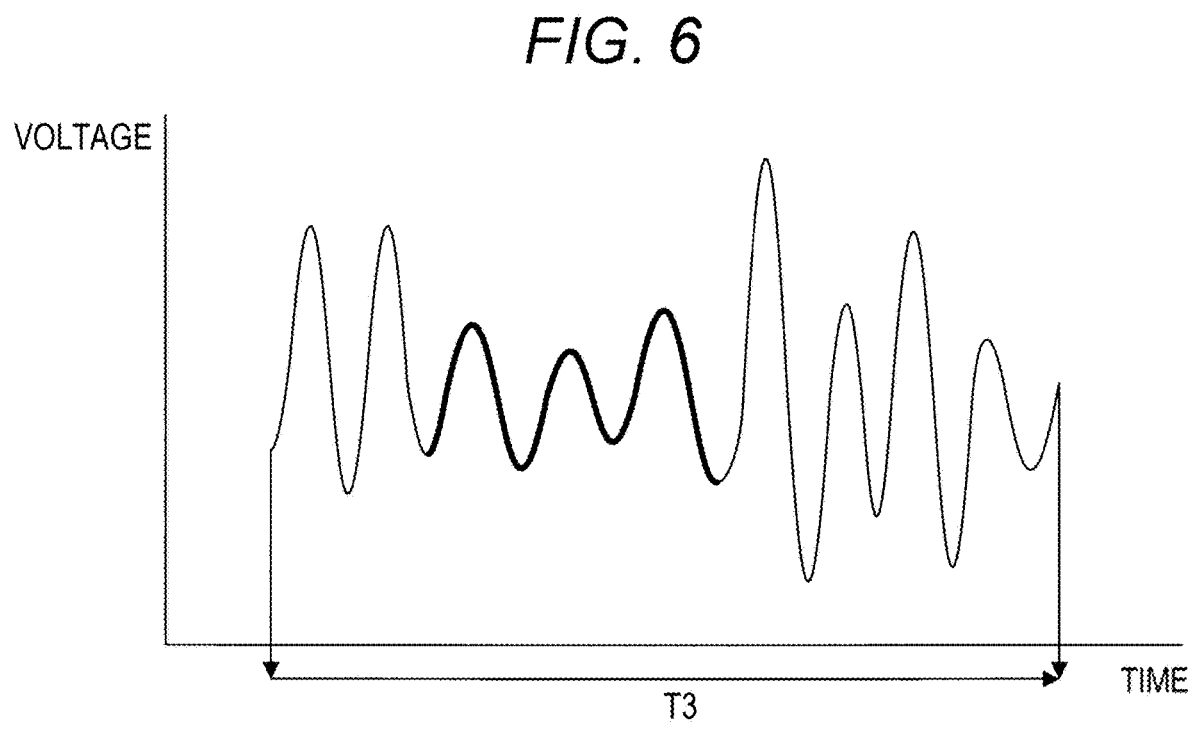

FIG. 6 is a diagram illustrating an example of a method of calculating the third score. FIG. 6 illustrates an example of a photoplethysmographic signal, which contains a signal waveform portion that is identified as high-precision pulses indicated by the bold line and some other signal waveform portions except the high-precision pulses. In the graph of FIG. 6, the vertical axis and the horizontal axis represent the same parameters as in FIG. 2.

The third score calculation function 33 performs the procedure same as that of generating the template to separate a user's photoplethysmographic signal into individual pulses and subjects the separated pulses to the normalization process. The third score calculation function 33 then calculates the degree to which each pulse generated as a result of the normalization process is matched with the template. More specifically, the third score calculation function 33 calculates a correlation coefficient between each pulse generated as a result of the normalization process and the template. Each correlation coefficient may be calculated using, for example, template matching, Euclidean distance, image matching, and some other image processes. The third score calculation function 33 then extracts, as high-precision pulses, from all the pulses generated as a result of the normalization process, pulses having a correlation coefficient equal to or more than a predetermined value (e.g., 0.95). The third score calculation function 33 then calculates, as the third score, a proportion of high-precision pulses to the pulses generated as a result of the normalization process. More specifically, the third score is calculated as H/I, where the number of pulses identified as the high-precision pulses is denoted by H, and the number of pulses per unit time is denoted by I. In this case, the third score increases as the number of high-precision pulses increases; in other words, the third score decreases as the number of high-precision pulses decreases. Therefore, a case where a condition for a predetermined threshold in the third score is satisfied can be regarded as a case where the third score is more than the preset threshold.

Alternatively, the third score calculation function 33 may extract a segment identified as the high-precision pulse from the user's photoplethysmographic signal, per unit time T3 and then may measure his/her pulse rate or other medical data from the extracted segment. In this case, the third score calculation function 33 may extract the segment indicated by the bold line containing a signal waveform suitable for the template by matching the user's photoplethysmographic signal with the template. The third score calculation function 33 then stores, in the storage unit 20, data area of the extracted high-precision pulses. The control unit 30 then measures the pulse rate and some other medical data from the area containing the high-precision pulses stored in the storage unit 20. It should be noted that another external device, rather than the server 100, may measure the pulse rate or other medical data.

With the above configuration, the third score calculation function 33 compares each pulse contained in the acquired photoplethysmographic signal and the template generated in advance, thereby calculating the proportion of the high-precision pulses as a third score.

It should be noted that the control unit 30 does not necessarily have to calculate all of the first score, the second score, and the third score. In this case, the control unit 30 intentionally calculates only one score out of the first score, the second score, and the third score.

Next, a description will be given below of a method of evaluating whether it is possible to extract the pulse rate and other medical data from the photoplethysmographic signal, based on the first score, the second score, and the third score.

The score evaluation function 34 determines whether it is possible to extract the pulse rate and other medical data from the acquired photoplethysmographic signal, based on the first score, the second score, and the third score as well as threshold presets for the respective scores.

The thresholds preset for the respective scores are set in the first score calculation function 31, the second score calculation function 32, and the third score calculation function 33. In this case, the control unit 30 may adjust each threshold, based on medical viewpoints, such as domain knowledge.

The first score can be used as an index indicating the distorted proportion of the acquired photoplethysmographic signal. As the first score increases, the photoplethysmographic signal is further distorted. It is thus more difficult to extract the pulse rate and other medical data from the photoplethysmographic signal. Therefore, the score evaluation function 34 determines whether the calculated first score is equal to or less than the threshold preset for the first score. More specifically, when the first score is less than the preset threshold, the score evaluation function 34 determines that the condition for the threshold of the first score is satisfied.

The second score can be used as an index indicating whether the acquired photoplethysmographic signal has periodicity synchronized with a pulsation. As the second score decreases, the periodicity of the photoplethysmographic signal synchronized with the pulsation decreases. It is thus more difficult to extract the pulse rate and other medical data from the photoplethysmographic signal. Therefore, the score evaluation function 34 determines whether the calculated second score is equal to or more than the threshold preset for the second score. More specifically, when the second score is more than the preset threshold, the score evaluation function 34 determines that the condition for the threshold of the second score is satisfied.

The third score can be used as an index indicating a proportion of the high-precision pulses contained in the acquired photoplethysmographic signal. As the third score decreases, the number of high-precision pulses contained in the photoplethysmographic signal decreases. It is thus smore difficult to extract the pulse rate and other medical data from the photoplethysmographic signal. Therefore, the score evaluation function 34 determines whether the calculated third score is equal to or more than the threshold preset for the third score. More specifically, when the third score is more than the preset threshold, the score evaluation function 34 determines that the condition for the threshold of the third score is satisfied.

When the first score, the second score, and the third score satisfy the conditions for the thresholds thereof, the score evaluation function 34 determines that it is possible to extract the pulse rate and other medical data from the acquired photoplethysmographic signal.

When at least one of the first score, the second score, and the third score does not satisfy the condition for the threshold thereof, the score evaluation function 34 determines that it is impossible to extract the pulse rate and other medical data from the acquired photoplethysmographic signal.

It should be noted that the score evaluation function 34 may intentionally use only one score out of the first score, the second score, and the third score. In this case, the score evaluation function 34 may determine whether it is possible to extract the pulse rate and other medical data from the acquired photoplethysmographic signal, based on any given score and the thresholds preset for this score.

Figure 7:
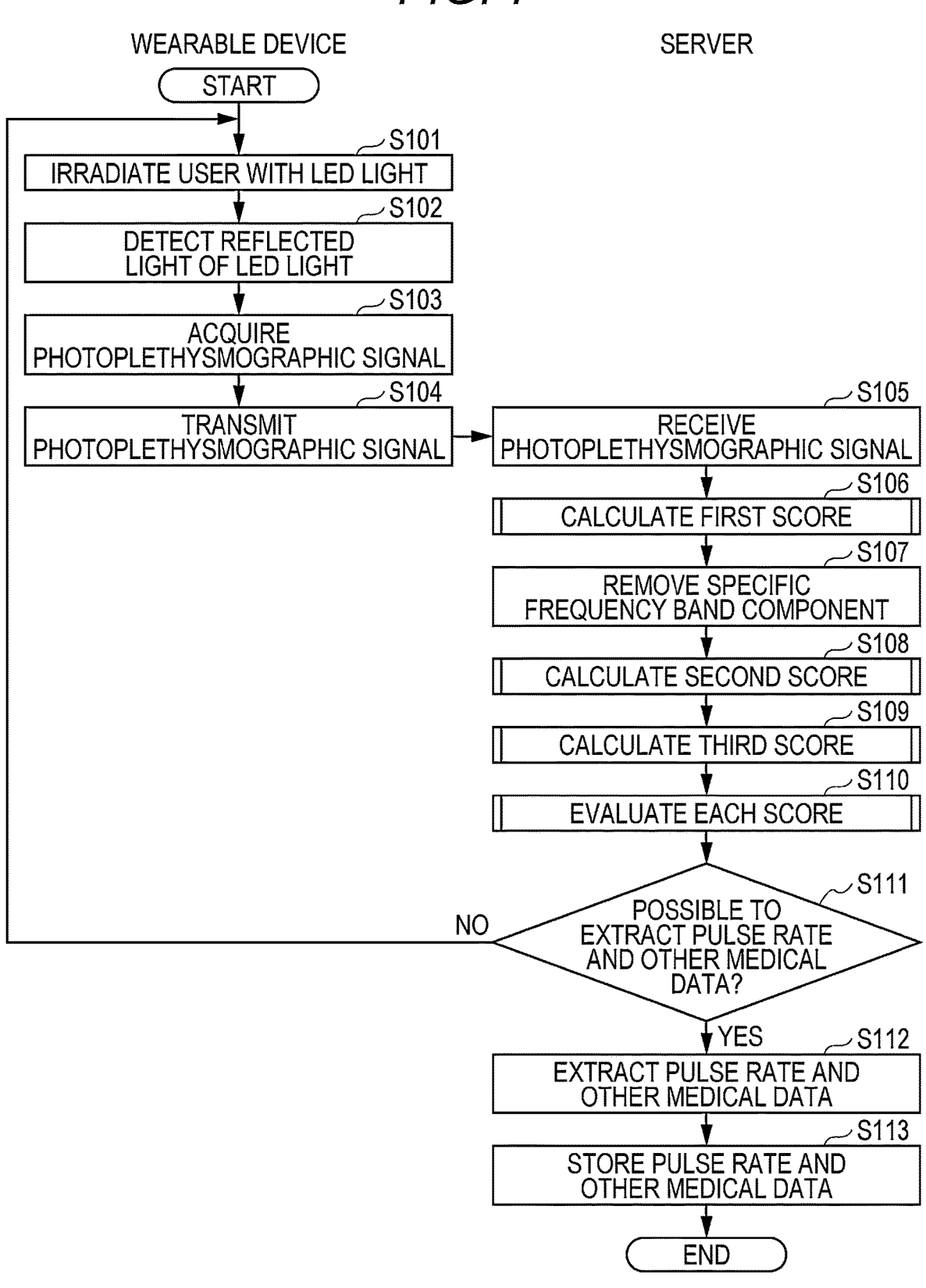
FIG. 7 is a flowchart illustrating an information process to be performed by the accuracy score calculation system for a photoplethysmographic signal.

FIG. 7 is a flowchart illustrating an information process to be performed by the accuracy score calculation system 1. The control unit 151 in the wearable device 150 controls the light emitting unit 153 to irradiate a user's arm or other body part with LED light (step S101). The control unit 151 then controls the light receiving unit 154 to detect t reflected light of the LED light with which the user is irradiated (step S102). The control unit 151 then acquires a photoplethysmographic signal from the detected reflected light by using the data processing unit 155 (step S103). The control unit 151 then controls the communication unit 156 to transmit the acquired photoplethysmographic signal to the server 100 (step S104).

The control unit 30 in the server 100 acquires the photoplethysmographic signal that has been transmitted by the wearable device 150 (step S105).

The control unit 30 executes a subroutine for calculating the first score by using the first score calculation function 31 (step S106). More specifically, the first score calculation function 31 calculates the distorted proportion of the acquired photoplethysmographic signal.

The control unit 30 removes specific frequency band components contained in the received photoplethysmographic signal by using an existing technique with a low-pass filter, a high-pass filter, a band-pass filter, and some other elements (step S107).

The control unit 30 executes a subroutine for calculating the second score by using the second score calculation function 32 (step S108). More specifically, the second score calculation function 32 calculates correction values from the photoplethysmographic signal and an envelope curve based on the photoplethysmographic signal and then performs autocorrelation analysis by using the calculated correction values.

The control unit 30 executes a subroutine for calculating the third score by using the third score calculation function 33 (step S109). More specifically, the third score calculation function 33 compares the acquired photoplethysmographic signal with the template prepared in advance and generated from the photoplethysmographic signal, thereby calculating the proportion of high-precision pulses.

The control unit 30 executes, by using the score calculation function 35, a subroutine for evaluating each of the scores calculated by the first score calculation function 31, the second score calculation function 32, and the third score calculation function 33 (step S110). More specifically, the score calculation function 35 determines whether it is possible to extract the pulse rate and other medical data from the acquired photoplethysmographic signal, based on the first score, the second score, and the third score as well as the thresholds preset for the respective scores.

Based on the determination result at step S110, the control unit 30 determines whether it is possible to extract the pulse rate and other medical data from the photoplethysmographic signal (step S111). When determining that it is possible to extract the pulse rate or other medical data from the acquired photoplethysmographic signal (YES at step S111), the control unit 30 extracts the pulse rate or other data from the photoplethysmographic signal (step S112). The control unit 30 stores the extracted pulse rate and other medical data in the storage unit 20 (step S113) and then concludes this process.

When determining that it is impossible to extract the pulse rate and other medical data from the acquired photoplethysmographic signal (NO at step S111), the control unit 30 returns this process to step S101.

Steps S106 through S111 may be performed for each of signal waveform portions of the photoplethysmographic signal, and Steps S112 and S113 may be performed only for the signal waveforms that satisfy the criteria. In that case, the control unit 30 may divide the photoplethysmographic signal into the signal waveform portions after performing S105, like the segments A and B shown in FIG. 2.

It should be noted that the procedures for calculating the first score (step S106) to the third score (step S109) may be performed in a different order and that the plurality of processes may be performed in parallel with one another.

Figure 8:
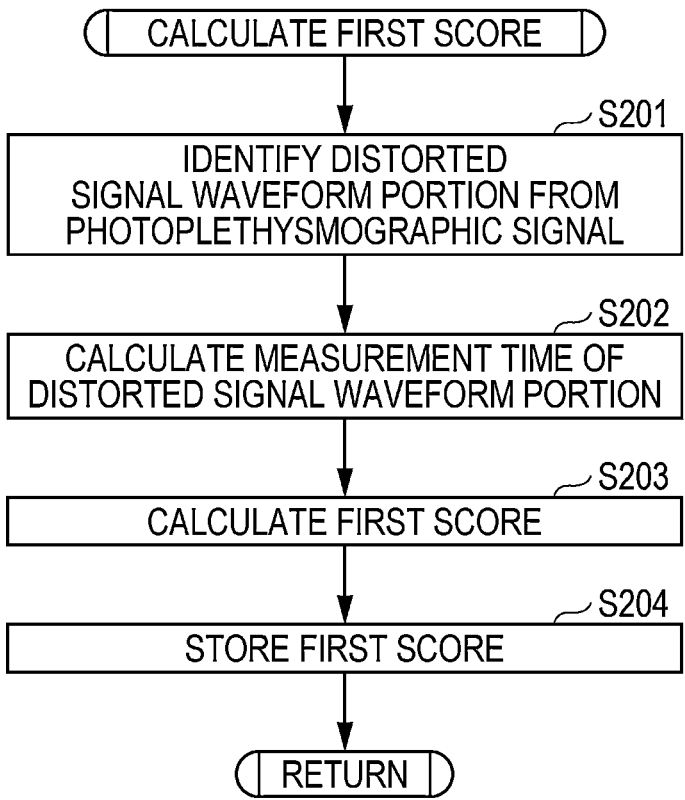
FIG. 8 is a flowchart illustrating a process of calculating the first score.

FIG. 8 is a flowchart illustrating a process of calculating the first score. Details of the subroutine related to step S106 will be described below. The first score calculation function 31 checks the acquired photoplethysmographic signal against a preset upper-limit voltage value, thereby identifying rectangular waveform portions (e.g., C, D, and E in FIG. 3) of the signal waveform (step S201). More specifically, the first score calculation function 31 identifies segments in which voltage values exceeding the preset upper-limit voltage value have been measured. The first score calculation function 31 then calculates times (e.g., c, d, and e) over which the voltage values of the photoplethysmographic signal exceed the upper-limit voltage value, based on the time at which the photoplethysmographic signal is acquired (step S202). The first score calculation function 31 then calculates, as the first score, a proportion of the portions in which the signal waveform has a rectangular waveform to the measured photoplethysmographic signal (step S203). More specifically, the first score calculation function 31 divides the total of the times (e.g., c, d, and e) over which the voltage value exceeding the preset upper-limit voltage value is detected by the total time (e.g., T1) when the photoplethysmographic signal is acquired. The first score calculation function 31 then stores the calculated first score in the storage unit 20 (step S204). After having stored the first score in the storage unit 20, the control unit 30 returns this process to step S107.

It should be noted that, when the calculated first score is equal to or more than a preset value, the first score calculation function 31 may transmit an instruction to the wearable device 150 to decrease the output of the LED light source.

It should be noted that, when the calculated first score is equal to or more than a preset value, the first score calculation function 31 may determine that it is impossible to use the acquired photoplethysmographic signal and then may not perform the subsequent process steps.

Figure 9:
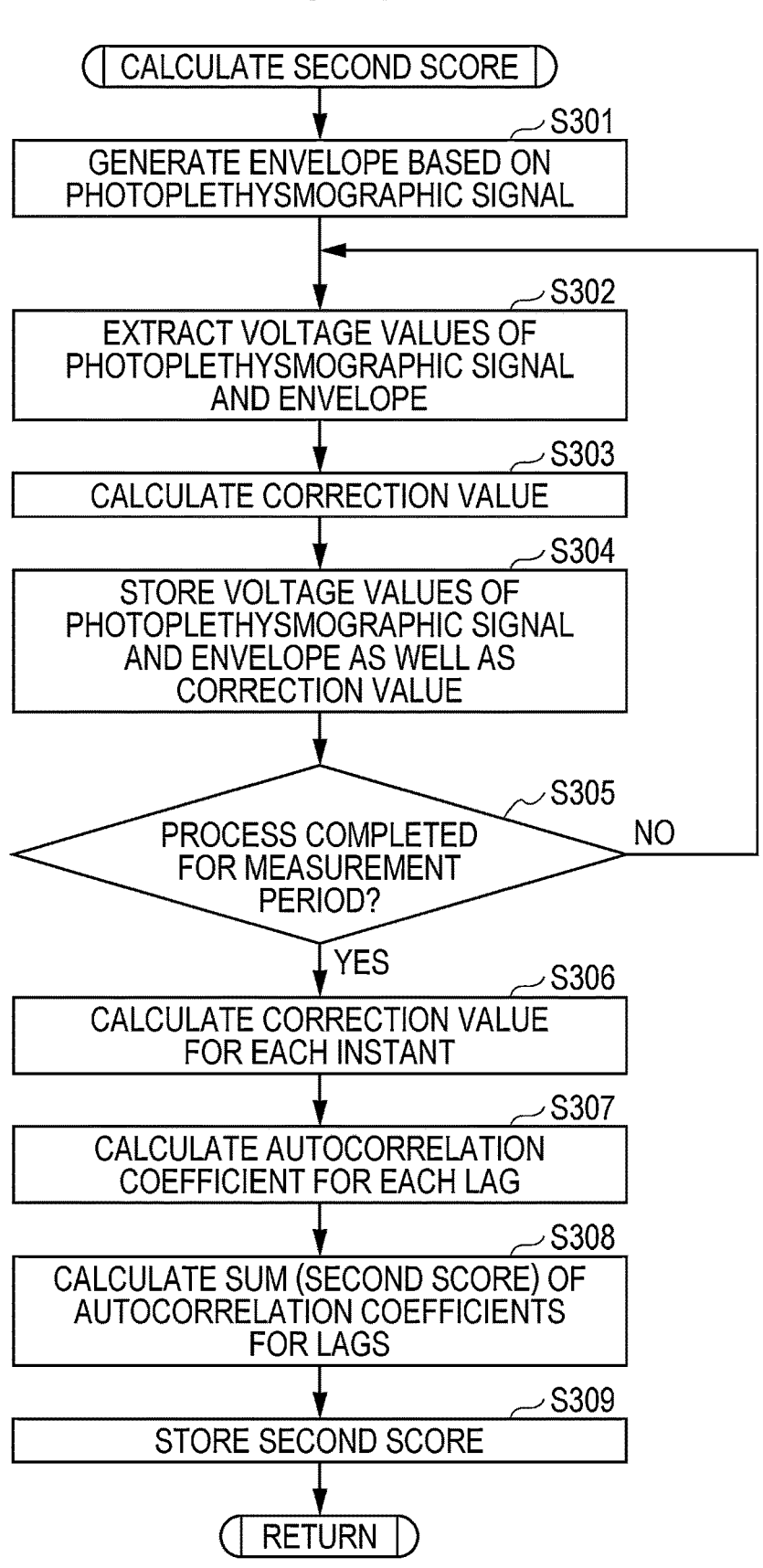
FIG. 9 is a flowchart illustrating a process of calculating the second score.

FIG. 9 is a flowchart illustrating a process of calculating the second score. Details of the subroutine related to step S108 will be described below. The second score calculation function 32 generates an envelope curve based on the photoplethysmographic signal that has been processed through the band pass filter (step S301). The envelope curve is generated, for example, by rectifying and smoothing the photoplethysmographic signal or by performing Hilbert transform thereon.

The second score calculation function 32 extracts voltage values of the photoplethysmographic signal and the envelope curve at a specific time (step S302). More specifically, the second score calculation function 32 extracts the voltage values (e.g., f and g in FIG. 4A) of the photoplethysmographic signal and the envelope curve at the specific time (e.g., t2). The second score calculation function 32 then calculates a correction value obtained by dividing the voltage value of the photoplethysmographic signal by the voltage value of the envelope curve (step S303). More specifically, the second score calculation function 32 divides the voltage value (e.g., f) of the photoplethysmographic signal at the specific time (e.g., t2) by the voltage value (e.g., g) of the envelope curve at the specific time. The second score calculation function 32 then stores, in the storage unit 20, the voltage values of the photoplethysmographic signal and the envelope curve, as well as the correction value (step S304). The second score calculation function 32 then determines whether the process at steps S302 to S304 has been completed for the period (T2) over which the photoplethysmographic signal has been measured (step S305). When the process at steps S302 to S304 has been completed for the specific period (YES at step S305), the second score calculation function 32 calculates a correction value for each time by using the correction value stored in the storage unit 20 (step S306). The second score calculation function 32 then performs autocorrelation analysis by using the correction value for each time, thereby calculating an autocorrelation coefficient for each lag (step S307). The second score calculation function 32 calculates the sum of the autocorrelation coefficients as the second score (step S308). The second score calculation function 32 then stores the calculated second score in the storage unit 20 (step S309). After having stored the second score in the storage unit 20, the control unit 30 returns this process to step S109.

When the process at steps S302 to S304 is not completed for the specific period (NO at step S305), the second score calculation function 32 returns this processing to step S302.

It should be noted that, when the calculated second score is equal to or less than the preset value, the second score calculation function 32 may determine that it is impossible to use the acquired photoplethysmographic signal and then may not perform the subsequent operations.

Figure 10:
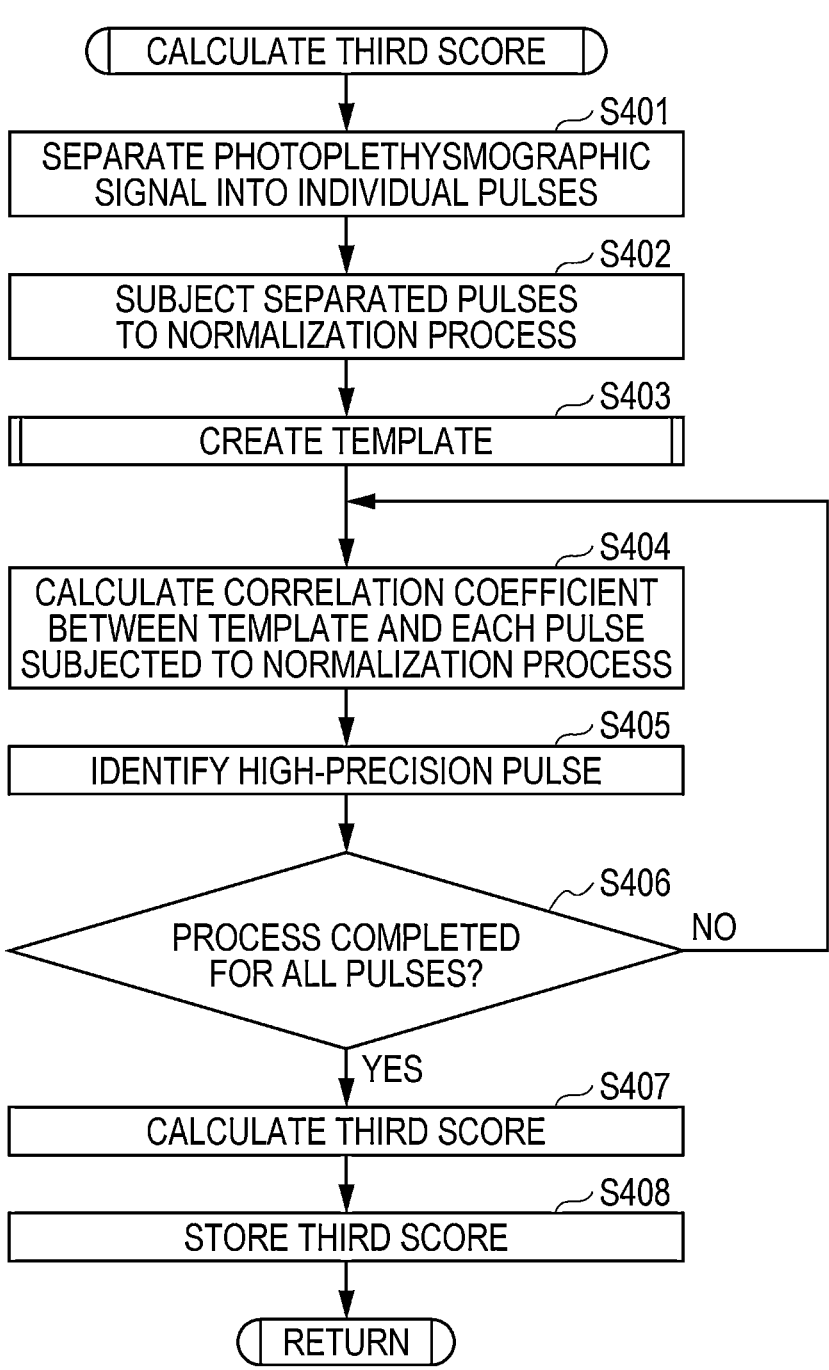
FIG. 10 is a flowchart illustrating a process of calculating the third score.

FIG. 10 is a flowchart illustrating a process of calculating the third score. Details of the subroutine related to step S109 will be described below. The third score calculation function 33 separates the photoplethysmographic signal into individual pulses (step S401). More specifically, the third score calculation function 33 regards, as the pulses, segments present between two adjacent valleys in the photoplethysmographic signal that has been acquired from the user and then separates the photoplethysmographic signal into the pulses. The third score calculation function 33 then subjects the separated pulses to the normalization process (step S402).

The control unit 30 executes the subroutine for generating a template by using the third score calculation function 33 (step S403). More specifically, the third score calculation function 33 generates the template by using a noiseless photoplethysmographic signal prepared in advance.

The third score calculation function 33 calculates a correlation coefficient between each of the pulses that have been subjected to the normalization process and the generated template (step S404). Each correlation coefficient may be calculated using, for example, template matching, Euclidean distance, image matching, and some other image processes. The third score calculation function 33 selects, from the pulses that have been subjected to the normalization process, pulses each having a correlation coefficient equal to or more than a predetermined value (e.g., 0.95) and then identifies the selected pulses as the high-precision pulses (step S405). The third score calculation function 33 then determines whether the process at steps S404 to S405 has been completed for all the pulses that have been subjected to the normalization process (step S406). When determining that the process at steps S404 to S405 has been completed for all the pulses subjected to the normalization process (YES at step S406), the third score calculation function 33 calculates, as the third score, a proportion of the high-precision pulses to all the pulses subjected to the normalization process (step S407). The control unit 30 then stores the third score in the storage unit 20 (step S408). After having stored the third score in the storage unit 20, the control unit 30 returns this process to step S110.

When determining that the process at steps S404 to S405 has not yet been completed for all the pulses subjected to the normalization process (NO at step S406), the third score calculation function 33 returns this process to step S404.

It should be noted that, when the calculated third score is equal to or less than a preset value, the third score calculation function 33 may determine that it is impossible to use the acquired photoplethysmographic signal and then may not perform the subsequent operations.

Figure 11:
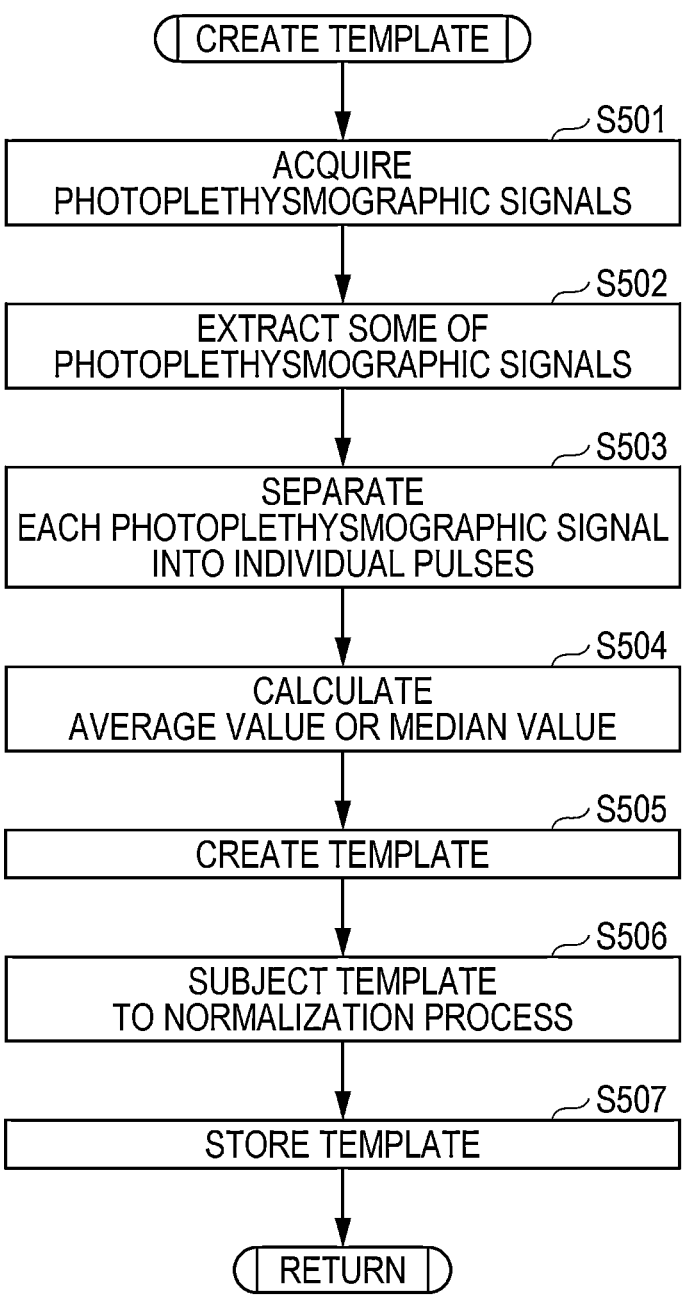
FIG. 11 is a flowchart illustrating a method of generating the template.

FIG. 11 is a flowchart illustrating a method of generating the template. Details of the subroutine related to step S403 will be described below. The third score calculation function 33 acquires a plurality of noiseless photoplethysmographic signals from the storage unit 20 (step S501). For example, the control unit 30 may acquire the plurality of noiseless photoplethysmographic signals in advance through a network, may process the acquired photoplethysmographic signals with a band pass filter, and may store the processed photoplethysmographic signals in the storage unit 20. The process with the band pass filter may be performed immediately before the template is generated. The third score calculation function 33 then extracts some (e.g., three samples) of the acquired photoplethysmographic signals therefrom, based on predetermined criteria (step S502). The predetermined criteria are set based on domain knowledge and medical viewpoints, for example. The third score calculation function 33 then separates each extracted photoplethysmographic signal into individual pulses (step S503). The pulse separation method may be the same as in step S401. The third score calculation function 33 combines the separated pulses together and then calculates an average value, a median value, or some other statistical values therefrom (step S504). The third score calculation function 33 then generates a template from the separated pulses by using the calculated average value, the median value, or the other statistical values (step S505). The third score calculation function 33 then subjects the generated template to the normalization process (step S506). As a result of the normalization, for example, the voltage value of each pulse is converted into a range of 0 to 1, whereas the time when each pulse is acquired is converted into a range of 0 to 100. The third score calculation function 33 then stores, in the storage unit 20, the template generated as a result of the normalization process (step S507). After having stored the template in the storage unit 20, the control unit 30 returns this process to step S404.

The subroutine for generating the template may be performed before the third score is calculated.

Figure 12:
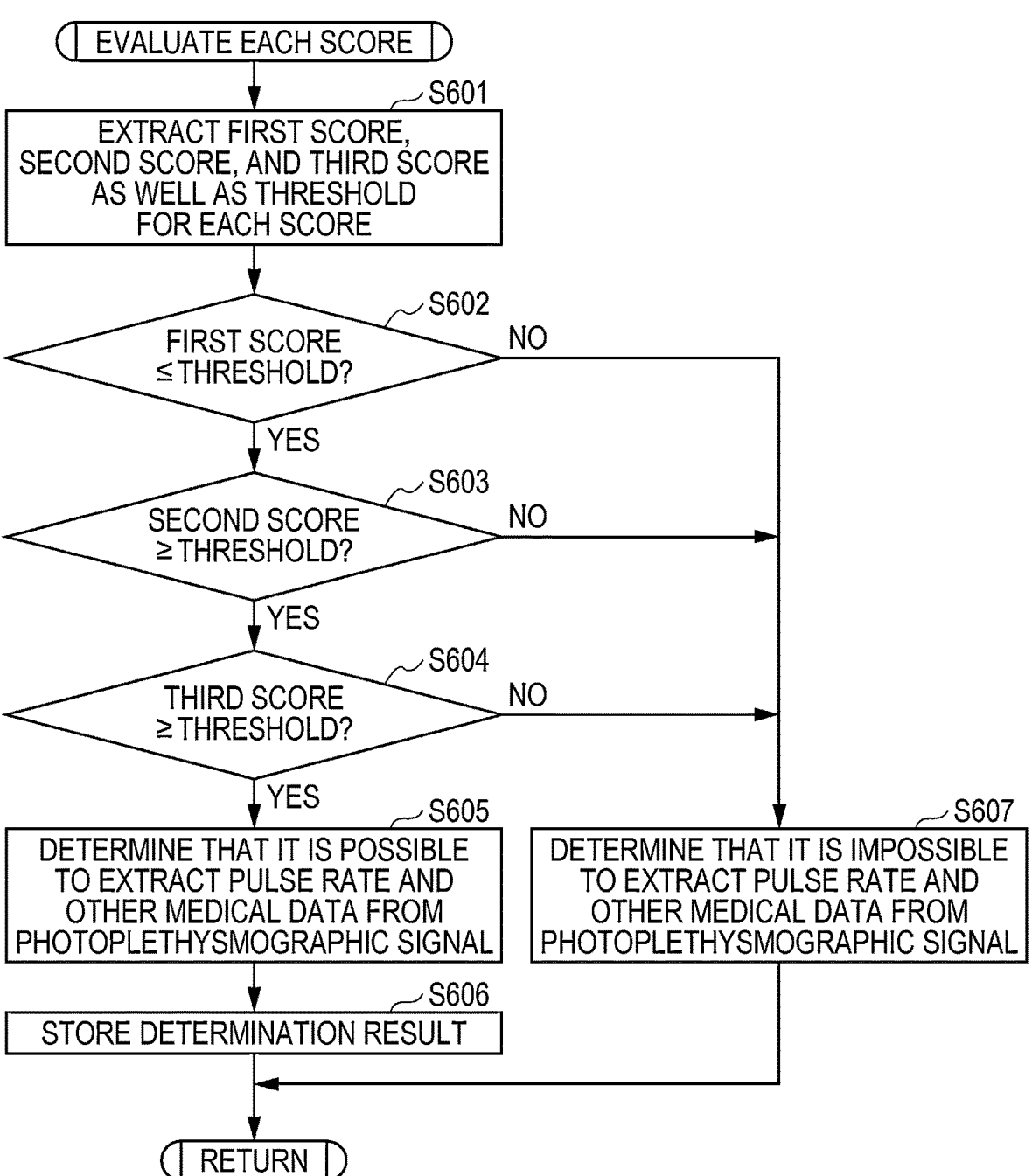
FIG. 12 is a flowchart illustrating a method of evaluating each score.

FIG. 12 is a flowchart illustrating a method of evaluating each score. Details of the subroutine related to step S110 will be described below. The score evaluation function 34 extracts, from the storage unit 20, the first score, the second score, and the third score as well as a threshold for each score (step S601). The score evaluation function 34 then determines whether the first score is equal to or less than the preset threshold (step S602). When determining that the first score is equal to or less than the threshold (YES at step S602), the score evaluation function 34, in turn, determines whether the second score is equal to or more than the preset threshold (step S603). When determining that the second score is equal to or more than the threshold (YES at step S603), the score evaluation function 34, in turn, determines whether the third score is equal to or more than the preset threshold (step S604). When determining that the third score is equal to or more than the threshold (YES at step S604), the score evaluation function 34 determines that it is possible to extract the pulse rate or some other medical data from the acquired photoplethysmographic signal (step S605). The control unit 30 then stores the above determination results in the storage unit 20 (step S606). After having stored the template in the storage unit 20, the control unit 30 returns this process to step S111.

When determining that the first score is equal to or more than the threshold (NO at step S602), the control unit 30 determines that it is impossible to extract the pulse rate and other medical data from the acquired photoplethysmographic signal (step S607). The control unit 30 then returns this process to step S111.

When determining that the second score is equal to or less than the threshold (NO at step S603), the control unit 30 determines that it is impossible to extract the pulse rate and other medical data from the acquired photoplethysmographic signal (step S607). The control unit 30 then returns this process to step S111.

When determining that the third score is equal to or less than the threshold (NO at step S604), the control unit 30 determines that it is impossible to extract the pulse rate and other medical data from the acquired photoplethysmographic signal (step S607). The control unit 30 then returns this process to step S111.

It should be noted that the score evaluation function 34 can change the order in which steps S602 to S604 are to be performed.

When determining that it is possible to extract the pulse rate and other medical data from the photoplethysmographic signal, the control unit 30 may link each determination result to original data of the photoplethysmographic signals used for the first score, the second score, and the third score and then store each determination result and the original data in the storage unit 20. In this case, the control unit 30 can share each determination result and the original data of the photoplethysmographic signal with an external analysis device, via the communication unit 10.

The score evaluation function 34 does not necessarily have to use all of the first score, the second score, and the third score. In other words, the score evaluation function 34 may use only one score to determine whether it is possible to extract the pulse rate and other medical data from the photoplethysmographic signal.

With the above configuration, the score evaluation function 34 can determine whether it is possible to extract the pulse rate and other medical data from the photoplethysmographic signal, based on the first score, the second score, and the third score as well as the threshold preset for each score. Moreover, the control unit 30 can extract a portion of the photoplethysmographic signal in which the pulse wave has been appropriately measured, by using the score evaluation function 34.

It should be construed that the embodiments disclosed herein are illustrative in all respects rather than restrictive. The scope of the present invention should be defined by the claims rather than the above meaning, and is intended to include all conceivable modifications and variations within the meaning and scope equivalent to the claims.

Some or all of the subject matters described in the respective embodiments can be combined together. In addition, some or all of the independent claims and their dependent claims described in the "what is claimed is" can be combined together, regardless of their dependent relationships. Furthermore, a form (multiple dependent claim form) in which a claim dependent on two or more other claims is described is used in the "what is claimed is"; however, the claim form is not limited thereto. The present invention may be described using a form in which a multiple dependent claim is dependent on at least one multiple dependent claim.

What is claimed is:

1. A method for obtaining photoplethysmographic data suitable for medical measurement, the method comprising:

emitting light from a photoplethysmographic sensor toward a body of a patient, and converting the light reflected by or passing through the body and received by the sensor for a particular period into a voltage signal indicating variation of voltage in the period;

calculating one or more scores for each of one or more portions of the voltage signal using voltage values thereof;

generating data corresponding to one of the portions, the one or more scores of which satisfy a predetermined condition; and storing in a memory the generated data as the photoplethysmographic data suitable for the medical measurement, wherein the one or more scores include a second score representing periodicity of a waveform in each portion of the voltage signal, and calculating includes determining an envelope curve of each portion of the voltage signal and performing an autocorrelation analysis on waveform data obtained by dividing the voltage values of each portion of the voltage signal by voltage values of the envelope curve.

2. The method according to claim 1, wherein calculating includes calculating a first score representing a degree of distortion of each portion of the voltage signal using the voltage values thereof and a predetermined upper limit of voltage variation.

3. The method according to claim 2, wherein the predetermined condition is satisfied when the first score is smaller than a first threshold.

4. The method according to claim 2, further comprising:

generating a waveform image for each portion of the voltage signal, and the first score is calculated using the generated image.

5. The method according to claim 1, wherein the predetermined condition is satisfied when the second score is greater than a second threshold.

6. The method according to claim 1, further comprising:

storing a reference waveform in the memory, wherein calculating includes calculating a third score representing similarity between each portion of the voltage signal and the reference waveform stored in the memory.

7. The method according to claim 6, wherein the predetermined condition is satisfied when the third score is greater than a third threshold.

8. A medical system comprising:

a photoplethysmographic sensor attachable to a body of a patient, and configured to emit light toward the body, and convert the light reflected by or passing through the body and received for a particular period into a voltage signal indicating variation of voltage in the period; and an information processing apparatus comprising:

an interface circuit connectable to the sensor, a memory, and a processor configured to:

acquire the voltage signal from the sensor through the interface circuit, calculate one or more scores for each of one or more portions of the voltage signal using voltage values thereof, generate data corresponding to one of the portions, the one or more scores of which satisfy a predetermined condition, and store in the memory the generated data as photoplethysmographic data suitable for medical measurement, wherein the one or more scores include a second score representing periodicity of a waveform in each portion of the voltage signal, and the processor is further configured to:

determine an envelope curve of each portion of the voltage signal, and perform an autocorrelation analysis on waveform data obtained by dividing the voltage values of each portion of the voltage signal by voltage values of the envelope curve.

9. The medical system according to claim 8, wherein the processor is configured to acquire a pulse rate of the patient using the data stored in the memory.

10. The medical system according to claim 8, wherein the processor calculates the score representing a degree of distortion of each portion of the voltage signal using the voltage values thereof and a predetermined upper limit of voltage variation.

11. The medical system according to claim 10, wherein the predetermined condition is satisfied when the score is smaller than a first threshold.

12. The medical system according to claim 10, wherein the processor is configured to:

generate a waveform image for each portion of the voltage signal, and calculate the score using the generated image.

13. The medical system according to claim 8, wherein the predetermined condition is satisfied when the score is greater than a second threshold.

14. A non-transitory computer readable medium storing a program causing a computer to execute a method for obtaining photoplethysmographic data suitable for medical measurement, the method comprising:

emitting light from a photoplethysmographic sensor toward a body of a patient, and converting the light reflected by or passing through the body and received by the sensor for a particular period into a voltage signal indicating variation of voltage in the period;

calculating one or more scores for each of one or more portions of the voltage signal using voltage values thereof;

generating data corresponding to one of the portions, the one or more scores of which satisfy a predetermined condition; and storing, in a memory of the computer, the generated data as the photoplethysmographic data suitable for the medical measurement, wherein the one or more scores include a second score representing periodicity of a waveform in each portion of the voltage signal, and calculating includes determining an envelope curve of each portion of the voltage signal and performing an autocorrelation analysis on waveform data obtained by dividing the voltage values of each portion of the voltage signal by voltage values of the envelope curve.

* * * * *